United States Patent [19]

Lakin

[11] 4,379,261
[45] Apr. 5, 1983

[54] ROTATING MAGNETIC FIELD DEVICE FOR DETECTING CRACKS IN METAL

[76] Inventor: Kenneth M. Lakin, 2601 Oakwood Rd., Ames, Iowa 50010

[21] Appl. No.: 185,968

[22] Filed: Sep. 10, 1980

[51] Int. Cl.³ .................... G01N 27/90; G01R 33/12
[52] U.S. Cl. .................................... 324/240; 324/232; 324/233
[58] Field of Search ............. 324/217, 218, 220, 221, 324/227, 228, 232–235, 238–243

[56] References Cited

U.S. PATENT DOCUMENTS

| | | | |
|---|---|---|---|
| 2,467,306 | 4/1949 | Habig | 324/242 |
| 2,558,485 | 6/1951 | Gow | 324/233 X |
| 3,056,920 | 10/1962 | Herrald | 324/221 |
| 3,109,139 | 10/1963 | Branker | 324/240 |
| 3,359,495 | 12/1967 | McMaster et al. | 324/235 |
| 3,449,664 | 6/1969 | Smith | 324/235 |
| 3,609,531 | 9/1971 | Forster | 324/232 X |
| 3,855,530 | 12/1974 | Fuji et al. | 324/216 X |
| 4,155,455 | 5/1979 | Spierer et al. | 324/232 X |

FOREIGN PATENT DOCUMENTS

| | | | |
|---|---|---|---|
| 1307213 | 9/1962 | France | 324/240 |
| 715946 | 2/1980 | U.S.S.R. | 324/228 |

Primary Examiner—Gerard R. Strecker

[57] ABSTRACT

An eddy current type of inspection device having input signal coils on cores radially arranged around a center and having outer ends of the cores which rest against a surface of a metal assembly to be tested for defects. The input coils are energized by an AC signal of different phase for each respective coil so that a rotating magnetic field is produced in the assembly being tested. An output sensor coil is mounted at the center of the tester immediately adjacent to such test surface for coupling out a signal induced from the rotating field. A specific embodiment has three coils physically spaced 120° apart, for energizing by a three-phase power source.

14 Claims, 11 Drawing Figures

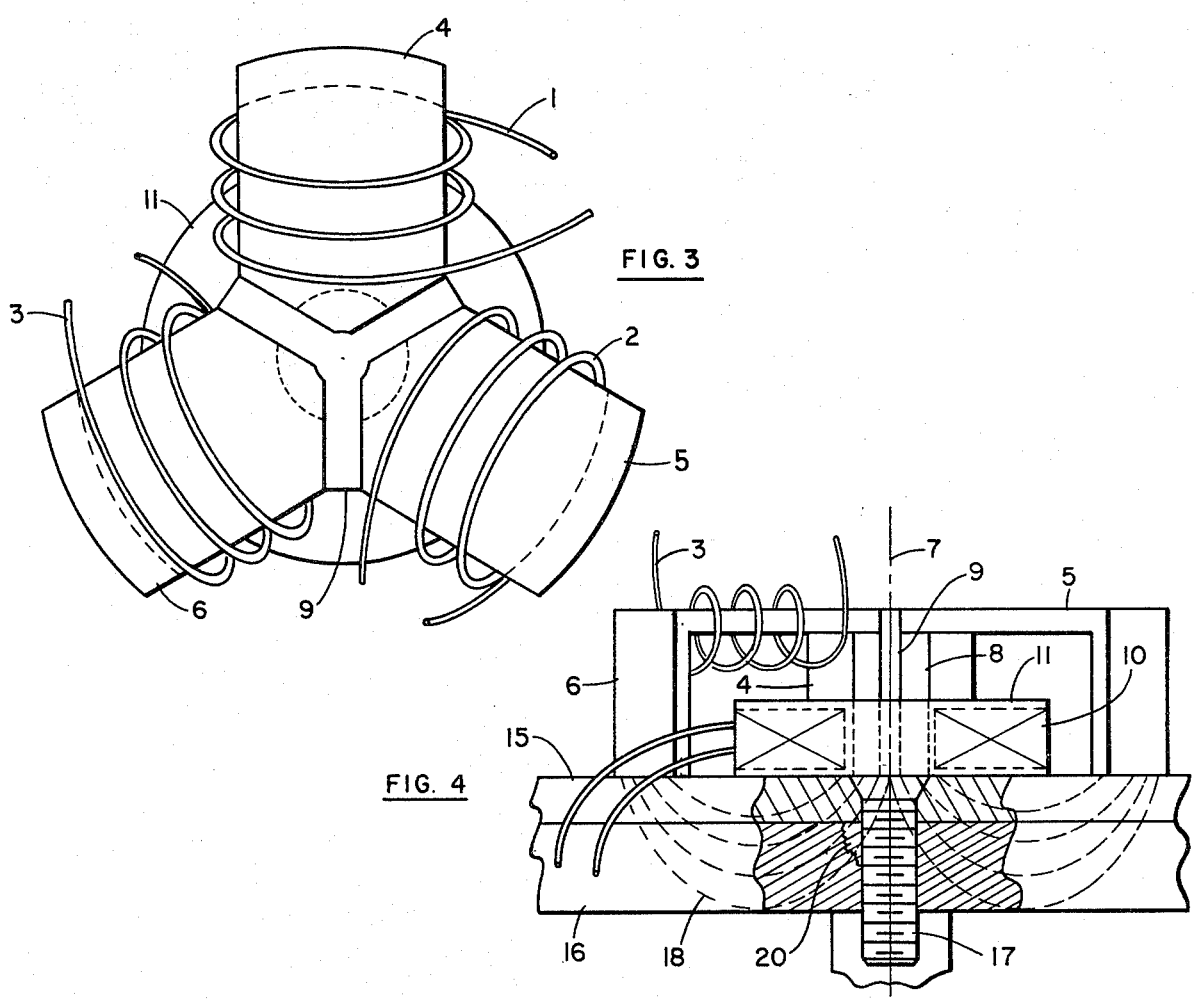
FIG. 3
FIG. 4
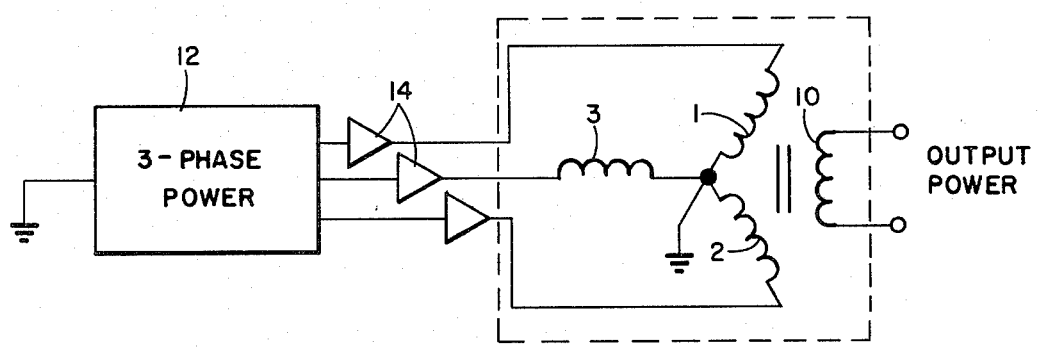
FIG. 5
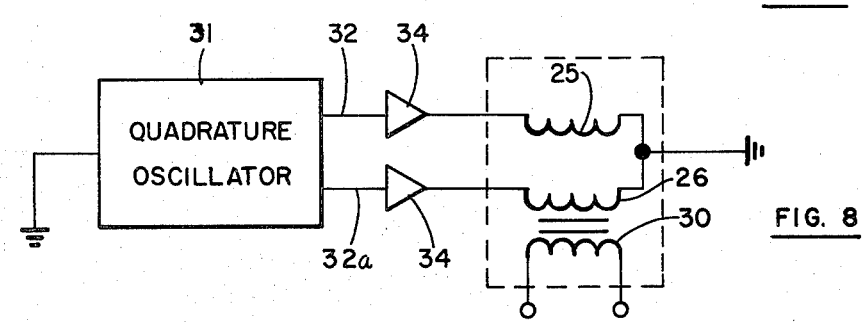
FIG. 8

ROTATING MAGNETIC FIELD DEVICE FOR DETECTING CRACKS IN METAL

BACKGROUND OF THE INVENTION

1. Field of the Invention

The present invention relates to non-destructive testing, and more particularly, to an eddy current means and method for detecting cracks in metal components such as the material around fastener holes.

In the aircraft industry, for example, it is known that fatigue cracks develop during the lifetime of components which repeatedly go through cycles of stress in normal operation. One particular location of such cracks which presents a serious problem because of their invisibility is in the holes around fasteners such as rivets, screws, and the like, particularly in the second layer under the fastener. For instance, in the large C-5A U.S. Air Force transport, there are approximately 17,000 critical fastener locations per aircraft.

2. Description of the Prior Art

Eddy current methods have been used to find these cracks when they have become quite large, by removing the fastener, and rotating an eddy current probe in the hole to determine if a crack is present. If no crack exists, a new fastener is installed. If a crack is found, the hole is reworked by enlarging it and then a new, larger size, fastener is installed, or a threaded insert may be installed in some cases.

Ultrasonic inspection methods have also been tried, without fastener removal, but this method has been unable to penetrate to inspect the second or lower layer of material under the fastener.

U.S. Pat. No. 3,855,530 to Fuji et al discloses the use of two coils wound on respectively perpendicular cores crossing at the center to provide two pairs of magnetic poles intersecting each other when the coils are energized on alternate half-cycles of a power supply voltage. The device can indicate flaws in a plane magnetic member by the positioning of magnetic powder spread on the member surface. This device does not actually produce eddy currents for the purposes used in an eddy current testing method.

U.S. Pat. No. 3,609,531 to Forster describes an eddy current probe that is effectively mechanically scanned along pipe for detecting cracks.

U.S. Pat. No. 4,155,455 to Spierer et al similarly makes use of a conventional eddy current test probe positioned adjacent to small magnetic material parts which are physically rotated while being tested for defects.

U.S. Pat. No. 2,558,485 to Gow shows a coaxial cable testing system wherein a three-phase rotating magnetic field is used to check the position of the center conductor of the cable when placed between the tips of the salient poles. No eddy current is generated, nor is there any crack detection.

In none of these patents is there found a teaching of detecting a crack particularly around the hole of an installed fastener, or in the second layer of material held together under the head of a fastener, or of scanning a test piece with an electrically rotating field to search for defects.

While it is possible that more pertinent prior art exists, Applicant's search is believed to have been conducted with a conscientious effort to locate and evaluate the most relevant art available at the time, but this statement is not to be construed as a representation that no more pertinent art exists.

Thus it is an object of this invention to provide a means and method of detecting small fatigue cracks in the second layer of sheet metal structure, for example.

Because of the very great number of fastener locations to be periodically inspected in an aircraft, another object of the present invention is to provide a testing method which is fast.

Still another object is to provide an eddy current inspection system which is inherently less sensitive to lift-off effects than prior known systems, i.e., minor and unavoidable variations in the position of the testing probe on the article or part being inspected. Such effects cause errors in the output indications from conventional mechanically scanned probes.

SUMMARY OF THE INVENTION

Briefly, my invention comprises the use of a plural-coil driver producing a rotating electromagnetic field which is coupled to the metal being inspected for cracks. The driver is preferably centered over a fastener location, and the rotating field scans the adjacent volume for cracks around the fastener hole with no motion of the driver itself. A cooperating pick-up or sensor coil detects an eddy current anomaly representing a crack and furnishes a signal usable for a display or other indication. Various designs and numbers of driver coils, together with appropriate electrical drive signals thereto, can be employed, along with various sensor coils. For instance, three driver coils wound on respective cores positioned at 120° angles to each other can be supplied with three-phase alternating current, and a single pancake type sensor coil may be positioned centrally of the driver coils and parallel to the member being tested immediately adjacent thereto. The cores preferably have leg ends in contact with the surface of the member under test.

BRIEF DESCRIPTION OF THE DRAWINGS

FIG. 3 is a plan view of the device of FIG. 1.

FIG. 4 is an elevation view of the same device, showing it in inspection position over an installed fastener.

FIG. 5 is an electrical schematic diagram of the device in FIGS. 1-4, also showing its input equipment.

FIG. 8 is an electrical schematic of an inspection system using the device of FIGS. 6 and 7.

DESCRIPTION OF THE PREFERRED EMBODIMENTS

Figure 1:
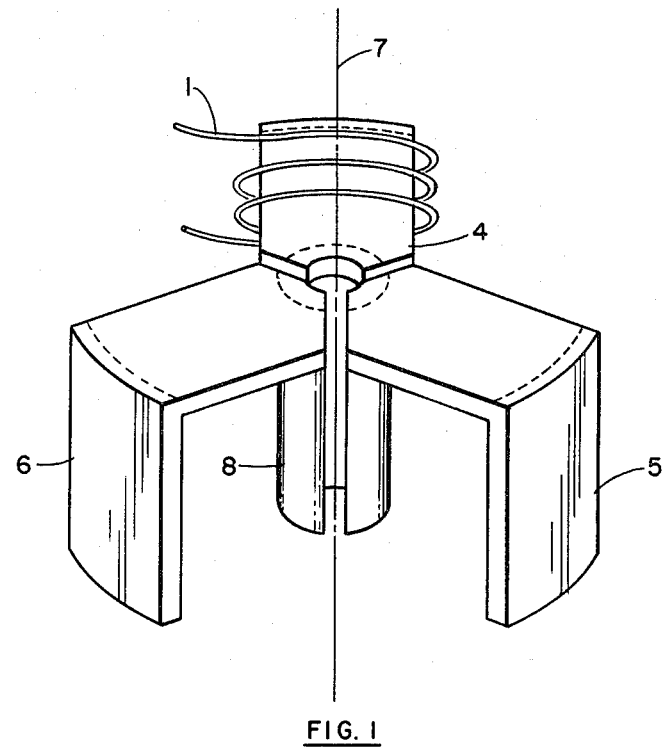
FIG. 1 is a top perspective view of a preferred embodiment of this inspection device using three driver or input coils, with the sensor or output coil omitted for clarity.
Figure 2:
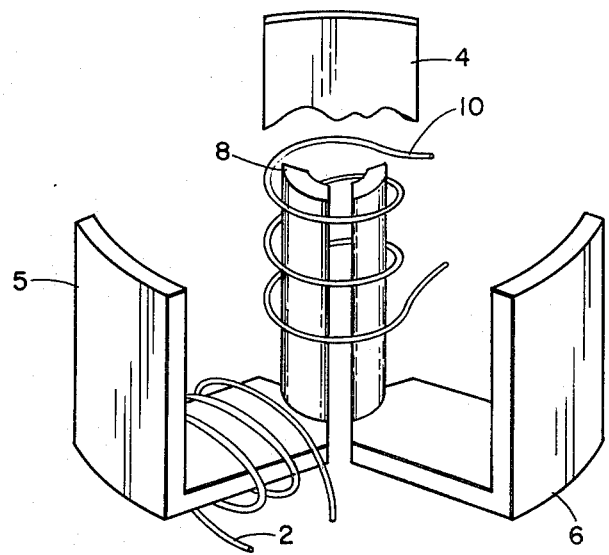
FIG. 2 is a bottom perspective view of the device of FIG. 1, partly cut away, including the sensor coil in pictorial fashion.

FIGS. 1-4 show one preferred arrangment of this invention. Three drive coils 1, 2 and 3 are wound on three magnetic cores 4, 5 and 6 which are substantially U-shaped and radially arranged equi-angularly about a central vertical axis 7 so that an inner leg 8 of each core is parallel to the axis 7. The inner legs 8 are greatly reduced in width just adjacent to the central axis 7. The core material may be ferrite, for example. The ends of all the core legs are in a common plane so that the whole assembly rests flat on a surface such as in FIG. 4. The assembly is held together by a suitable potting compound 9 (FIGS. 3 and 4) with the inner legs 8 of the cores slightly separated from each other. The potting 9 is omitted from FIGS. 1 and 2 for clarity.

A single sensor coil 10 is wound on a horizontal bobbin 11 (FIGS. 3 and 4) and bonded around the inner legs 8 of the cores. The sensor coil 10 is positioned as close as possible to the surface of the component to be inspected, as shown in FIG. 4.

To secure a rotating electromagnetic field, the input or drive coils 1, 2 and 3 are energized as shown in FIG. 5. The three phase output windings of a three-phase power supply 12 are respectively connected through driver amplifiers 14, if desired, to one end of each of the drive coils 1, 2 and 3. The opposite ends of the drive coils are connected together to ground.

The structure to be tested in FIG. 4 typically comprises a first or top layer surface 15, a second or bottom layer 16, and a fastener 17. For examining the volume of metal around this fastener 17, the test assembly is first placed with its vertical axis 7 centered over the fastener 17 and held stationary (or nearly stationary) while the AC drive signal is then put in operation. The applied magnetic field in the fastener joint structure is represented by flux lines 18, and the resulting eddy currents are detected by the sensor coil 10.

An output signal is taken from the leads of the sensor coil. If the test assembly were by itself, the signal picked up by sensor coil 10 from the drive coils alone would be zero due to the zero vector sum of the three flux contributions from the drive coils because the sensor coil effectively samples each of these fluxes. Now when the tester is positioned in place on a metal structure to be tested, the sensor coil voltage will also be zero if the flux induced by the eddy currents is perfectly symmetrical. This is the case with no cracks present. If, however, a crack 20 (FIG. 4) is present, the resulting asymmetry will cause a finite "error" voltage generally proportional in magnitude to the size of the crack. The phase of this error voltage from sensor coil 10 will indicate the angular location of the crack 20 around the fastener 17.

The error output voltage from sensor coil 10 may be amplified, conditioned and fed to a readout circuit (not shown) or to a display such as an oscilloscope for example. Such signal readout circuits and indicators are well known in the art.

Figure 6:
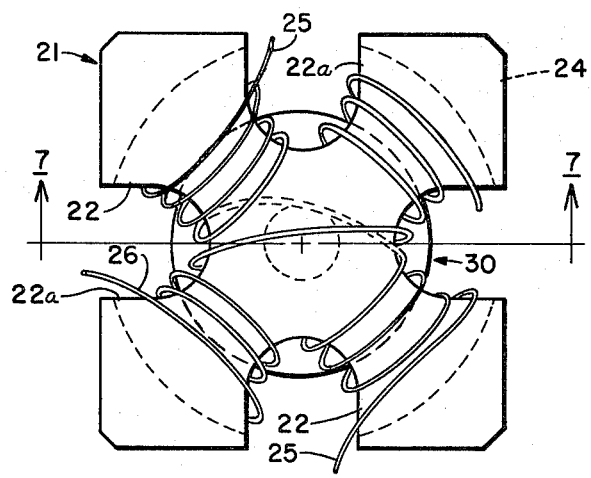
FIG. 6 is a plan view of another embodiment of this invention, showing an inspection assembly having two input coils wound on a crossed core.
Figure 7:
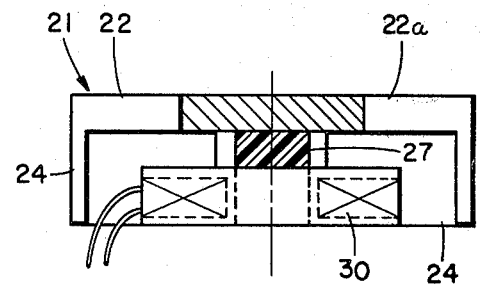
FIG. 7 is a cross section taken as indicated by broken line 7—7 in FIG. 6, with the drive coils omitted for clarity.

FIGS. 6 and 7 show another example of tester built in accordance with the present invention. A single core piece 21 having four spokes 22, 22a is provided, with a leg 24 at 90 degrees to the outer end of each spoke 22. A first continuously wound drive coil 25 is provided on one pair of opposite spokes 22, and a second similar drive coil 26 on the other two opposite spokes 22a. Thus each of the two drive coils 25 and 26 is symmetrical about the center of core piece 21 rather than being off-center of the entire core assembly as are the coils 1, 2 and 3 of FIG. 1. The core piece 21 is shaped to have relatively large-area leg ends to put in contact with the test surface, for maximum coupling of electromagnetic flux, and relatively small intermediate portions of the spokes 22 and 22a so that a maximum coil winding space is provided. Of couse the core 21 could comprise separate pieces bolted together, for example.

In this design of FIGS. 6 and 7, no inner or central legs of the magnetic core piece 21 are provided in contact with the material under test, although they could be. Instead, a plastic or other dielectric dowel 27 is bonded at the bottom center of core piece 21. A pick-up coil 30 is mounted on dowel 27 similarly to the sensor coil 10 of FIG. 4. For operation, the tester is again centered over the fastener hole to be tested, as in FIG. 4. Although the dowel 27 is illustrated herein as being plastic, it may be the same material as the magnetic core piece 21.

The rotating electromagnetic field for this two-coil device is provided as shown in FIG. 8. A quadrature oscillator 31 puts out two waveforms 90 degrees apart on output lines 32 and 32a. After proper power amplification in drivers 34, the drive signals are applied to one end of the respective first and second drive coils 25 and 26. The other ends of drive coils 25 and 26 are grounded. Thus some of the eddy current field passes horizontally through the fastener (such as 17 in FIG. 4) at any one instant and the vector representing this field is rotating about the center of the fastener. During one 360-degree rotation of the eddy current field, a single crack such as crack 20 in FIG. 4 will cause two strong perturbations (180° apart) in the output signal from the pick-up coil 30. The position of these "blips" on an otherwise zero output signal will indicate that the crack is at either x° or 180°+ x° around the fastener 17, and further probing treatment will distinguish one case from the other.

Figure 9:
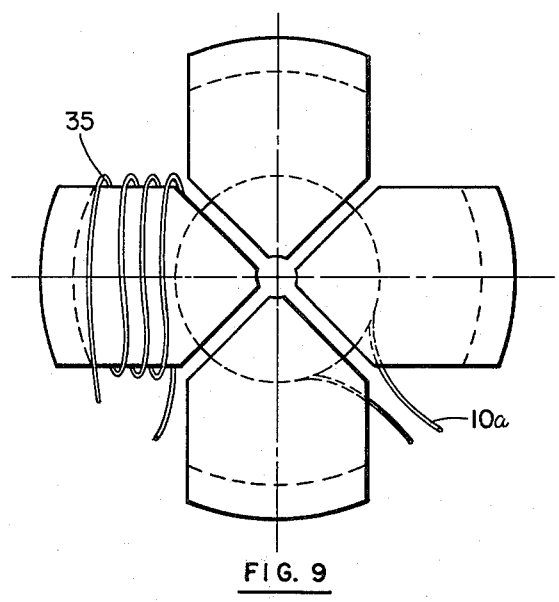
FIG. 9 is a plan view of another arrangement of this invention, showing four input coils.
Figure 10:
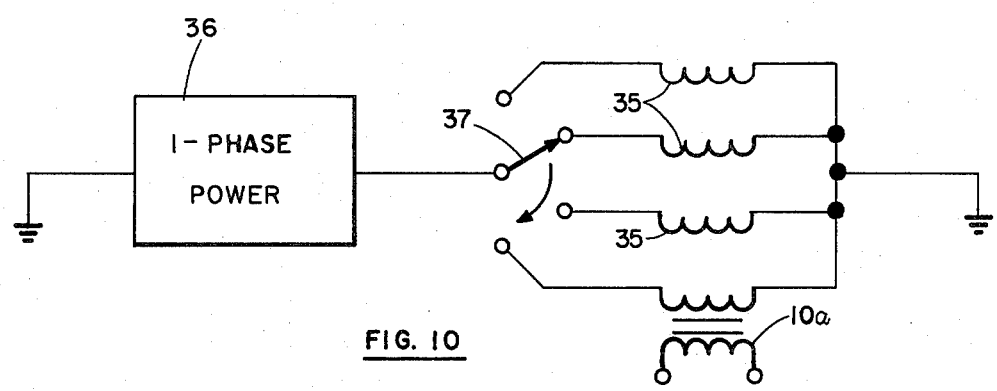
FIG. 10 is a schematic of an electrical system which may be used with the device of FIG. 9.

As an example of what other forms the present invention may take, FIG. 9 shows an arrangement similar to FIG. 1 but having four drive coils 35 instead of three. The field rotation for this embodiment may be accomplished by sequential switching as shown in FIG. 10. Here a single-phase power supply 36 has a four-position electronic switch 37 in its output. In operation, switch 37 is sequentially connected to one end of each of the four drive coils 35, while the other ends are grounded. This effectively rotates the electromagnetic field so that by correlating the output signal from the sensor coil 10a with a reference position of switch 37, the detection and location of a defect can be accomplished. In such an arrangement, the drive coils 35 are merely intermittently energized rather than continuously.

Figure 11:
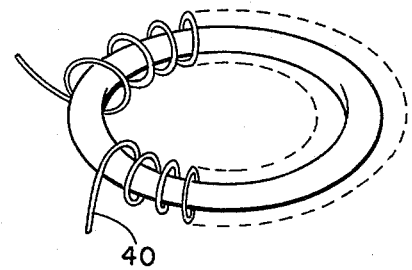
FIG. 11 is a perspective view of a toroidal coil which may be used in place of the form of sensor coil shown in FIGS. 2 and 4.

While only a pancake type of sensor coil 10 or 30 has been illustrated herein, the type of sensor coil winding may obviously be different. The sensor coils 10 and 30 respond best to vertical components of the flux field as existing in the central or inner core legs extending through the sensor coil. However, a toroidal type of sensor coil 40 as shown in FIG. 11 may be used if desired to pick up particularly the flux components in the plane of the toroid. A third form of sensor coil arrangement would be an assembly of three pick-up coils (not shown), each would in a different mutually perpendicular plane.

The center sensor coil 10 or 30 may be used to accurately center the test assembly over the fastener 17 when testing for cracks. The crack indicating circuitry may be switched out of circuit from the sensor coil 10 and a special oscillator signal of high frequency may be switched in. By including an impedance meter in circuit with the coil, this operation will detect the edge of the fastener hole, and a minimum output from the impedance circuit will indicate the centered position of the instrument. Then the centering circuit will be switched out or turned off, and the regular test output circuitry switched in to immediately indicate the test result at that location.

In the present invention, a low frequency drive signal of 700 to 1000 Hertz, for example, may be used. The switching rate for the embodiment of FIG. 10 may be from one to ten cycles per second, for example. Also, the various coil windings of this invention are preferably spaced apart at the center of the test assembly so that a high-density flux path is produced vertically through the said center. This achieves the advantage of an "off center" coil in finding deeper cracks.

The important principle is the rotating magnetic field in the part being tested, and the provision of associated means for detecting or measuring the eddy current disturbances resulting from a crack in relation to the corresponding direction of the magnetic field. The eddy current field scans the hole or the test region in a rotative manner.

By essentially eliminating problems due to lift-off and centering, which have in the past created errors that dominate the signals generated by the cracks themselves, the present invention has much greater sensitivity and ability to detect cracks in the second or bottom layer of material. This is in addition to the obvious speed advantage of this invention obtained by not having to remove the fastener to enable inspection.

Further, although being described herein in connection with only flush-head fasteners, it will be seen that my invention may likewise be adapted to situations where raised-head fasteners are employed.

While in order to comply with the statute, the invention has been described in language more or less specific as to structural features, it is to be understood that the invention is not limited to the specific features shown, but that the means and construction herein disclosed comprise the preferred mode of putting the invention into effect, and the invention is therefore claimed in any of its forms or modifications within the legitimate and valid scope of the appended claims.

What is claimed is

1. Eddy current inspection apparatus for detecting cracks in a metallic article having a flat surface, comprising:
   (a) a central magnetic core extending longitudinally along a central axis, the central core having two ends designated the first and second ends, respectively;
   (b) at least three L-shaped peripheral magnetic cores,
      (i) each peripheral core having first and second leg portions joined to form the two legs of an L-shaped member, the first leg portion being magnetically coupled to the first end of the central core and extending radially away from the central axis, and the second leg portion extending parallel to the central axis and terminating in a foot, and
      (ii) the feet of each of the peripheral cores and the second end of the central core being substantially coplanar;
   (c) a drive coil wound on each of the peripheral cores;
   (d) means for electrically energizing each drive coil with an alternating-current signal, the signals applied to the different drive coils having at least two different electrical phases so as to produce in the metallic article, when the feet of the peripheral cores are positioned abutting the surface of the article, a magnetic field rotating about the central axis;
   (e) a sensor coil wound on the central core; and
   (f) means for detecting the voltage appearing across the sensor coil, the value of the voltage indicating whether a crack exists in the metallic article.

2. Apparatus in accordance with claim 1 wherein said means for energizing said coils includes an AC power source having an output signal of different phase relation connected to each of said drive coils.

3. Apparatus in accordance with claim 1 wherein said means for energizing said coils includes selector switch means for cyclically connecting said coils to an AC power source in consecutive order around said central axis.

4. Apparatus in accordance with claim 1 wherein said cores are separate core pieces of generally U-shaped magnetic material arranged radially around said central axis with an inner leg of each said U-shaped piece being parallel to said axis, said pieces being bonded together by a potting compound, said sensor coil means comprising a sensor coil wound around said inner legs of said core pieces.

5. Apparatus in accordance with claim 1 wherein said cores comprise a single body of magnetic material having a plurality of radial spokes around which said coils are wound.

6. Apparatus in accordance with claim 1 wherein said means for energizing said coils comprises a multiphase AC power source equal in number of phases to the number of said coils, and means connecting each of the phase circuits of said source in consecutive manner to a different respective one of said coils.

7. Apparatus in accordance with claim 1 wherein there are three said cores substantially 120° apart around said axis, and including means for connecting said coils respectively to the three outputs of a three-phase electrical power source.

8. Apparatus in accordance with claim 1 including a dowel element fastened to the center of said plurality of cores along said central aixs, and wherein said sensor coil means comprises a pancake type coil wound aound said dowel and positioned substantially flush with said outer leg ends so as to lie immediately adjacent to the surface of said article under test.

9. Apparatus in accordance with claim 1 wherein said sensor coil means comprises a toroid centered on said central axis, and a toroidal coil wound on said toroid and positioned immediately adjacent to the surface of said article under test.

10. Apparatus in accordance with claim 1 wherein there are two said cores intersecting at substantially right angles, and including means for connecting said drive coils respectively to the two outputs of a quadrature oscillator.

11. Apparatus in accordance with claim 1 wherein said plurality of cores comprises three separate cores of generally U-shaped magnetic material arranged radially around said central axis substantially 120° apart, with an inner leg of each said U-shaped core being parallel to said axis, said cores being bonded together by a potting compound, wherein said means for energizing said coils comprises means for connecting said coils respectively to the three outputs of a three-phase electrical power source, and wherein said sensor coil means comprises a sensor coil wound around said inner legs of said cores.

12. Apparatus in accordance with claim 1 wherein said plurality of cores comprises four spokes of a single magnetic core piece, there being two of said drive coils each wound half on a respective one of said four spokes and half on the opposite respective spoke, and wherein said means for energizing said coils comprises means for connecting said two drive coils respectively to the two outputs of a quadrature oscillator.

13. Apparatus in accordance with claim 12 wherein said sensor coil means comprises a pancake type sensor coil, and means attaching said sensor coil to said core piece in a position to be parallel to said article under test.

14. Apparatus in accordance with claim 1 wherein said plurality of cores comprises four cores substantially 90° apart around said axis, and wherein said means for energizing said coils comprises selector switch means for cyclically connecting said coils to an AC power source in consecutive order around said central axis.

* * * * *